US010088395B2

(12) United States Patent
Schueler et al.

(10) Patent No.: US 10,088,395 B2
(45) Date of Patent: Oct. 2, 2018

(54) DEVICE FOR EXTRACTING VOLATILE COMPONENTS

(71) Applicant: CTC Analytics AG, Zwingen (CH)

(72) Inventors: Kai Heinrich Schueler, Hoffeld (CH);
Melchior Zumbach, Lenzburg (CH);
Stefan Anton Cretnik, Grellingen (CH)

(73) Assignee: CTC ANALYTICS AG, Zwingen (CH)

(*) Notice: Subject to any disclaimer, the term of this patent is extended or adjusted under 35 U.S.C. 154(b) by 342 days.

(21) Appl. No.: 15/135,001

(22) Filed: Apr. 21, 2016

(65) Prior Publication Data

US 2016/0320271 A1 Nov. 3, 2016

(30) Foreign Application Priority Data

May 1, 2015 (EP) .................................... 15001305

(51) Int. Cl.
*G01N 1/24* (2006.01)
*G01N 1/22* (2006.01)
(Continued)

(52) U.S. Cl.
CPC ............ *G01N 1/24* (2013.01); *G01N 1/2214* (2013.01); *G01N 1/2226* (2013.01); *G01N 30/12* (2013.01);
(Continued)

(58) Field of Classification Search
CPC ...... G01N 1/24; G01N 1/2214; G01N 1/2226; G01N 1/405; G01N 30/12;
(Continued)

(56) References Cited

U.S. PATENT DOCUMENTS 6,139,801 A * 10/2000 Kawachi ............. G01N 1/2273
422/110
6,365,107 B1 * 4/2002 Markelov ............ G01N 1/2226
422/63
(Continued)

FOREIGN PATENT DOCUMENTS

EP    0 590 932 A2    4/1994
EP    2 775 298 A1    9/2014

*Primary Examiner* — Lisa Caputo
*Assistant Examiner* — Nathaniel T Woodward
(74) *Attorney, Agent, or Firm* — Birch, Stewart, Kolasch & Birch, LLP

(57) ABSTRACT

The present application relates to a device for extracting volatile components from a sample received in a sample vessel, wherein the sample vessel is closed in a gas-tight manner. The device moreover has a discharge line and a supply line, which protrude into the sample vessel. The supply line comprises a first valve with which a flow of gas through the supply line can be throttled and/or interrupted. A suction opening of a pump is fluidically connected to the discharge line via a first fluid line, such that the pressure conditions in the device can be controlled by the capacity of the pump and by the setting of the first valve. A second fluid line fluidically connects the supply line to an output opening of the pump, such that sample vessel, supply line, discharge line and pump form a closed gas circuit. A trap element with at least one sorption material is fluidically connected to the first fluid line or the second fluid line.

12 Claims, 1 Drawing Sheet

(51) Int. Cl.
*G01N 30/12* (2006.01)
*G01N 1/40* (2006.01)

(52) U.S. Cl.
CPC ..... *G01N 1/405* (2013.01); *G01N 2001/2229* (2013.01); *G01N 2001/2282* (2013.01); *G01N 2001/247* (2013.01); *G01N 2030/121* (2013.01)

(58) Field of Classification Search
CPC ... G01N 2001/2229; G01N 2001/2282; G01N 2001/247; G01N 2030/121
USPC .............................................. 73/864.34, 200
See application file for complete search history.

(56) References Cited

U.S. PATENT DOCUMENTS

| | | | |
|---|---|---|---|
| 6,391,096 B1 * | 5/2002 | Waters | B01D 19/0031 73/19.02 |
| 6,395,560 B1 * | 5/2002 | Markelov | G01N 1/2226 422/68.1 |
| 6,984,260 B2 * | 1/2006 | Atkinson | B01D 45/04 73/200 |
| 9,170,241 B2 * | 10/2015 | McCauley | G01N 30/16 |
| 2013/0233094 A1 * | 9/2013 | Meece | G01N 35/1097 73/863.83 |
| 2013/0315780 A1 * | 11/2013 | Cook | G01N 21/66 422/52 |

* cited by examiner

DEVICE FOR EXTRACTING VOLATILE COMPONENTS

TECHNICAL FIELD

The invention relates to a device for extracting a volatile component from a sample, in particular from a liquid sample.

PRIOR ART

Various devices are known in the prior art for extracting volatile components, for example volatile organic compounds (VOC), from a sample. It is desirable in particular to transfer volatile components from a sample to the gas phase and then collect the latter, for example in a column with suitable sorption material.

Particularly in the field of environmental analysis, extraction devices of this kind are used to detect contaminants in water samples or soil samples. The extracted volatile components are collected in a trap column and then volatilized from this by action of heat, wherein the volatile components are transferred to an analysis apparatus, in particular a gas chromatograph, where they can be separated, identified and also quantified.

The so-called purge and trap method has in particular become established in this field. In this method, an inert gas is passed through a sample. Volatile components transfer from the sample into the gas phase. These components are then collected on a suitable sorption material or in a cold trap. In the final expulsion step, the trap is heated such that the volatile components can be transferred to a gas chromatograph.

EP 0 590 932 A1 (Peters A.) discloses a trap system with a trap column, in particular for chromatography. The system comprises, among other things, a vacuum pump, which is connected via a valve to the output opening of the trap column and to the input opening of a separating column, and also a source of a carrier gas. When the vacuum pump is switched on, an analyte is sucked by the resulting underpressure into the trap column, which is designed as a cold trap. At the same time, the separating column is backflushed. Then, by separating the vacuum pump from the system and allowing the carrier gas to flow in through the input opening of the trap column and heating the latter, the molecules collected in the cold trap can be flushed into the separating column and then fed to a GC. The inner wall of the trap column can be coated with a porous polymer.

U.S. Pat. No. 6,395,560 B1 (Merkelov M.) describes a headspace device that can be used in a purge and trap method. The analyte withdrawn from the headspace by the carrier gas can be concentrated in a trap. Carrier gas and analyte that are not held back in the trap can either be released into the atmosphere or collected, for example in a helium trap.

U.S. Pat. No. 6,365,107 B1 relates to a headspace device in which a disturbance of the thermodynamic equilibrium in the sample vessel is not interrupted by the withdrawal of analyte. For this purpose, the device has two piston syringes, wherein a defined volume of analyte is withdrawn via a first piston syringe and, at the same time, the same volume of an inert gas is injected into the sample vessel by means of the second piston syringe.

An important disadvantage of existing purge-and-trap systems is that the inert gas used is released into the atmosphere. On the one hand, this gives rise to costs, since used inert gas is no longer available for further analyses, and, on the other hand, there is the danger that dissolved volatile substances not held back in the sorption material or in the cold trap contaminate the air in an analysis laboratory. Since these can in some cases be carcinogenic substances, the last point is a considerable disadvantage of the previously known purge-and-trap systems. Moreover, the loss of volatile substances can lead to an incorrect quantitative measurement. In addition, the extraction of the soluble components always takes place at an overpressure in the sample vessel, which generally leads to poorer outgassing of the soluble components.

DISCLOSURE OF THE INVENTION

The object of the invention is to make available a device which pertains to the technical field mentioned at the outset and with which the gas consumption and the contamination of the surrounding atmosphere with volatile components can be reduced.

The object is achieved by the features of claim 1. According to the invention, a device for extracting volatile components from a sample comprises a sample vessel for receiving the sample, wherein the sample vessel is closed in a gas-tight manner. Moreover, the device has a discharge line and a supply line, which protrude into the sample vessel. The supply line comprises a first valve with which a flow of gas through the supply line can be throttled and/or interrupted. A suction opening of a pump is fluidically connected to the discharge line via a first fluid line. A second fluid line fluidically connects the supply line to an output opening of the pump, such that sample vessel, supply line, discharge line and pump form a closed gas circuit. A trap element with at least one sorption material is fluidically connected to the first or second fluid line.

The gas consumption is considerably reduced by the device according to the invention. Moreover, contamination of the environment by soluble components not held back in the used trap element is prevented. During the extraction, the continuous suctioning of the gas has the effect that an underpressure is obtained in the sample vessel, which increases the outgassing of the volatile components. Since a closed gas circuit is present, the device has the further advantage that there is no limitation by a breakthrough capacity, i.e. an infinite volume of gas can in theory be conveyed through the trap element without extracted volatile substances being lost from the system. Moreover, the pressure conditions inside the sample vessel and the trap element can be controlled and changed by the capacity of the pump and of the first valve.

The sample is preferably present as a solid or liquid. A gas space, the so-called headspace, remains above the sample in the sample vessel. After the sample is introduced into the sample vessel, which is preferably made of glass or of a polymer resistant to chemicals, the sample vessel is closed in a gas-tight manner, for example with a stopper, cover, septum or the like.

The supply line and the discharge line can be formed on the sample vessel itself, for example in the form of connector stubs that can be connected to the fluid lines. Alternatively, the closure piece of the sample vessel can also have the supply line and the discharge line or can be connected to these. Moreover, it is also conceivable that the supply line and the discharge line are plugged into the sample vessel after the latter has been closed, for example through suitable openings. As a person skilled in the art will know, the attachment of the supply line and discharge line to the sample vessel must be made gas-tight with respect to the atmosphere.

The supply line preferably has a throttle valve with which a flow of gas into the sample vessel can be reduced or interrupted. Alternatively, the supply line can also have a shut-off valve with which the flow of gas can be interrupted. By means of this reduction or interruption of the gas flowing through the supply line into the sample vessel, an underpressure can be generated in the sample vessel via the pump, which promotes or accelerates the outgassing of the volatile components. Moreover, an overpressure can in this way be generated at the same time in the trap element, as a result of which the capacity of the trap element and therefore also the yield of the extraction can be increased.

The fluid lines can be present in any desired form, for example as hoses, capillaries, glass tubes, etc. Any pump suitable for conveying gas can be used as pump. A pump is particularly preferably used which permits a continuous delivery of gas, for example rotary piston pumps or peristaltic pumps. Alternatively, cyclical pumps such as piston pumps or diaphragm pumps can also be used. Suitable pumps are known to a person skilled in the art in this field.

The trap element has a suitable sorption material, for example a porous polymer based on 2,6-diphenyl-p-phenylene oxide, which is sold under the trade name Tenax® by Buchem BV. Depending on the nature of the substances to be extracted, a suitable sorption material can be used for the trap. Alternatively, a cold trap can also be used as the trap.

After the sample vessel has been closed, the device is preferably flooded with an inert gas such as helium, nitrogen, carbon dioxide or argon, with any air present being removed from the device via a valve.

Preferably, the trap element is connected releasably to the first fluid line or the second fluid line.

In the direction of flow of gas, the trap element can therefore be connected to the first or second fluid line upstream or downstream from the pump. Preferably, however, the trap element is connected to the second fluid line, i.e. downstream from the pump in the direction of flow of gas.

By virtue of the fact that the trap element is connected releasably to the first or second fluid line, the trap element can be released from the device and transported to an analysis apparatus, in particular to a gas chromatograph, after the volatile components have been extracted from the sample.

The releasable connection can be configured, for example, as a bayonet catch, as an injection port with septum, or by means of a flange or screw connection. Other suitable releasable connections are known to a person skilled in the art in the field of laboratory technology.

The first fluid line or the second fluid line preferably comprises two subsidiary fluid lines, wherein the trap element is arranged between these two subsidiary fluid lines. In a configuration of this kind, the gas flows completely through the trap element.

Alternatively, it is possible for the trap element to be connected only on one side to the fluid line, e.g. via a three-way valve. In this case, for example, the three-way valve can have an automatic switch, wherein the gas flow is conveyed into the trap element, which leads to an overpressure in the trap element and at the same time an underpressure in the sample vessel. The valve can then be switched such that the gas present in the trap element can flow into the sample vessel, in which case an underpressure is present in the trap element and an overpressure in the sample vessel, since the pump conveys gas continuously.

It is also conceivable that the trap element is arranged parallel to the fluid line, i.e. the stream of gas is divided via a valve, wherein one part of the stream of gas flows through the trap element, while a further part flows through the fluid line, after which both streams of gas are brought together again via a second valve.

The supply line preferably protrudes farther into the sample vessel than the discharge line, such that, when a liquid sample is received, the supply line protrudes into the liquid and the discharge line protrudes into a gas space above the liquid.

In this way, the device according to the invention can be used in a classical purge and trap method in which the solution equilibrium of the volatile components inside the liquid can be disturbed by bubbling the gas through, such that these volatile components can outgas from the liquid.

In the direction of flow of the closed gas circuit, a water trap is preferably arranged upstream from the trap element in the first fluid line or the second fluid line.

By means of the water trap, it is possible to remove from the stream of gas any water that would cause interference in a subsequent analysis of the volatile components held back in the trap element in a gas chromatograph. Common water traps are known to a person skilled in the art, for example through the use of molecular sieves. The water trap is in this case preferably arranged in such a way that the entire flow of gas passes through the water trap before flowing into the trap element.

The trap element preferably has at least one valve with which the trap element can be fluidically connected to an analysis apparatus, in particular to a gas chromatograph. In this way, the volatile components held back in the trap element can be transferred for analysis in a corresponding device.

The trap element preferably has a heating and/or cooling element. A heating element permits rapid and virtually complete desorption of volatile components held back in the trap element. By way of a cooling element, the temperature of the trap element can be reduced in the sense of a cold trap, in order to permit virtually complete retention of the volatile components in the trap element.

The supply line can preferably be fluidically connected to a gas reservoir via a second valve. In this way, prior to an extraction, the device can be flooded with a gas, in particular an inert gas. The gas reservoir can be present, for example, in the form of a gas bottle with a reducing valve, which can be connected via a line to the second valve of the supply line.

The trap element is preferably designed as a syringe, wherein a needle of the syringe is inserted into the second fluid line, and wherein the at least one sorption material is arranged in the barrel of the syringe.

Such a design of the trap element permits very simple transfer of the trap element from the device to an analysis apparatus. Moreover, in the desorption of volatile substances held back in the trap element, the volume injected into the analysis apparatus can be controlled very precisely, for example via the total volume of the syringe used, or via a piston arranged movably in the syringe.

Such trap elements are known in the prior art and are marketed by the applicant CTC Analytics under the name ITEX.

The present application further relates to a method for extracting a volatile component from a sample, in particular using a device as described above. In a first step of the method according to the invention, a sample is arranged in a sample vessel with a supply line and a discharge line, wherein the sample vessel is then closed in a gas-tight manner, in particular by a septum. Gas is then aspirated out of the sample vessel, or out of a gas space located above the sample, into the discharge line. The aspiration is effected via a pump connected to the discharge line via a first fluid line. The gas is conveyed by the pump into a second supply line, which is fluidically connected to the supply line. The gas is thus circulated in the sense of a closed gas circuit between sample vessel and pump. Volatile components of the sample are held back in a trap element fluidically connected to the first fluid line or the second fluid line.

The consumption of a carrier gas in an extraction method is greatly reduced by the method according to the invention, since the carrier gas is continuously circulated through the closed circuit. Moreover, a contamination of the environment by soluble components not held back in the used trap is prevented. Moreover, by virtue of the continuous aspiration and introduction of the gas, there is no overpressure in the sample vessel, which thus accelerates the outgassing of the volatile components. Since a closed gas circuit is present, the method has the further advantage that the trap element has as it were an infinite breakthrough capacity, i.e. an infinite volume of gas can in theory be conveyed through the trap element, without extracted volatile substances being able to escape from the trap element and being lost.

In the method according to the invention, the used device is advantageously flooded with an inert carrier gas after the sample vessel has been closed. The inert carrier gas can be introduced via a gas reservoir connectable to the device, e.g. via a valve.

A flow of gas in the closed gas circuit is preferably throttled or interrupted for a predetermined time by a first valve of the supply line, such that an underpressure arises in the sample vessel and an overpressure arises in the trap element.

By throttling or interrupting the flow of gas, the underpressure in the sample vessel and the overpressure in the trap element arise at the same time as a result of the gas output of the pump. Volatile components in the sample can be more easily outgassed by the underpressure, as a result of which the efficiency of the extraction is increased. The absorption efficiency is also briefly increased by the overpressure in the trap element.

The throttling or interruption of the flow of gas is preferably effected by an automatically controlled first valve. The first valve can be controlled by a suitable control unit. Particularly preferably, the flow of gas is throttled or interrupted at regular time intervals. Alternatively, other time intervals can also be chosen. Moreover, it is also possible to vary the intervals or the duration of the throttlings or of the interruptions in accordance with the gas pressure. For example, a throttling or interruption can be maintained until a predetermined maximum pressure is reached, whereupon the throttling or interruption is canceled until a predetermined minimum pressure is reached. Depending on the nature of the sample, of the trap element and of the volatile components to be extracted, the time and duration of the throttlings and interruptions can be correspondingly varied. Furthermore, the strength of the throttling can also be set and/or varied.

Particularly preferably, the method according to the invention is carried out using a device according to the above description, wherein the trap element used is a syringe which is connected to the first or the second fluid line.

In this embodiment of the method, a piston of the syringe is periodically driven to and fro. In this way, gas is sucked out of the gas flow into the barrel of the syringe and forced back out again, and sorption material present in the syringe is able to take up the volatile components.

In this embodiment of the method, the movement to and fro of the piston is particularly preferably coordinated with the throttling or interruption of the flow of gas through the first valve. The piston is preferably moved when the flow of gas is throttled or interrupted, as a result of which an extraction at a controlled overpressure is permitted.

The syringe can be connected to the first supply line or the second supply line via a three-way valve. The switching of the three-way valve is in this case coordinated with the periodic movement of the piston, such that the valve connects the syringe to the flow of gas on the discharge side when the piston is moved back and on the supply line side when the piston is moved forward.

Further advantageous embodiments and combinations of features of the invention will become clear from the following detailed description and from all of the patent claims.

BRIEF DESCRIPTION OF THE DRAWINGS

In the drawings used to explain the illustrative embodiment.

Identical parts in the figures are in principle provided with identical reference signs.

Ways of Implementing the Invention

Figure 1:
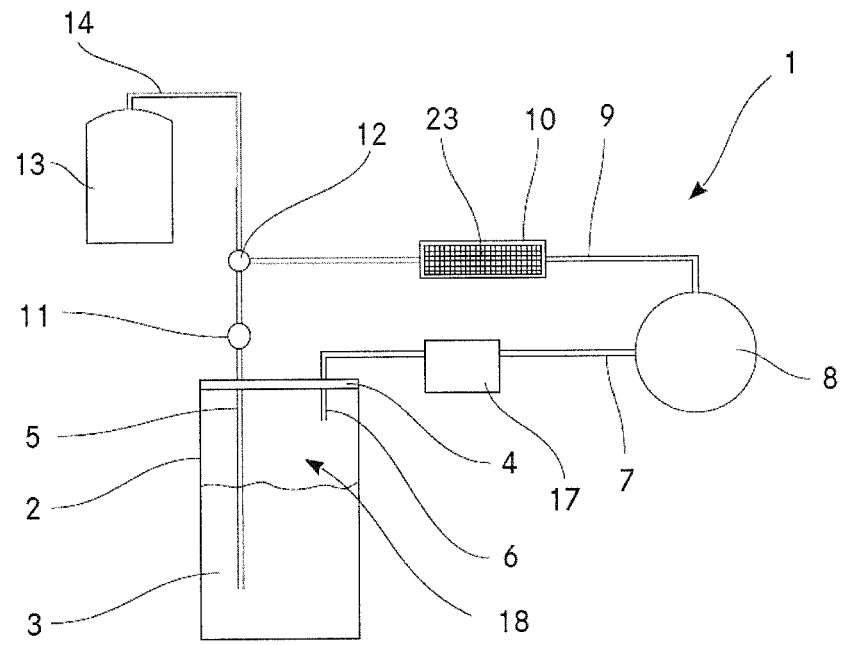
FIG. 1 shows a schematic view of a first embodiment of a device according to the invention.

FIG. 1 shows a schematic view of a first embodiment of a device 1 according to the invention. The device 1 has a sample vessel 3 which, in the embodiment shown, can be closed in a gas-tight manner by a cover 4. A liquid sample 3 is shown in the sample vessel 2. The liquid sample 3 is introduced into the sample vessel 2 in such a way that a gas space 18, the so-called headspace, forms between the liquid sample 3 and the cover 4. A supply line 5 and a discharge line 6 are inserted through the cover 4 into the sample vessel 2. The supply line 5 is arranged in such a way that it protrudes into the liquid sample 3, while the discharge line 6 protrudes into the gas space 18.

The discharge line 6 is connected to a suction opening of a pump 8 via a first fluid line 7. In the embodiment shown, a water trap 17 is integrated in the first fluid line. Gas from the gas space is sucked by the pump 8 through the discharge line 6 into the first fluid line 7, wherein the water trap 17 binds water, present in the gas, and moisture.

The pump 8 is connected at an output opening to a second fluid line 9, in which a trap element 10 is releasably integrated. The second fluid line connects the pump 8 to the supply line. By the operation of the pump 8, a closed gas circuit can be generated from the sample vessel 2 through the first fluid line 7 to the pump 8 and back through the second fluid line 9 to the sample vessel 2. The gas is introduced into the liquid sample 3 in the sample vessel 2. The gas then bubbles through the liquid sample 3 into the gas space 18, where it is sucked up through the discharge line 6. The solution equilibrium is disturbed by the bubbling through of the gas and by the continuous supply of gas into the gas space 18, such that volatile components located in the liquid sample 3 outgas into the gas space 18, where they are sucked up through the discharge line 6 and conveyed to the trap element 10.

In the embodiment shown, the trap element 10 is integrated in the second fluid line 9, i.e. the second fluid line 9 is present in two subsidiary lines, which are connected to each other via the trap element 10. The trap element 10 is thus connected in series to the second fluid line 9.

The supply line 5 has a first valve 11, with which the flow of gas through the supply line 5 can be throttled or interrupted. In this way, for a predetermined period of time, an underpressure can be generated in the gas space 18 in the sample vessel 2 and an overpressure can be generated in the trap element 10, since the pump 8 conveys gas continuously.

Arranged between the second fluid line 9 and the supply line 5 there is a second valve 12, to which a gas reservoir 13, shown in the present illustrative embodiment in the form of a gas canister, can be connected. The gas reservoir 13 is connected to the second valve 12 via a gas line 14.

Figure 2:
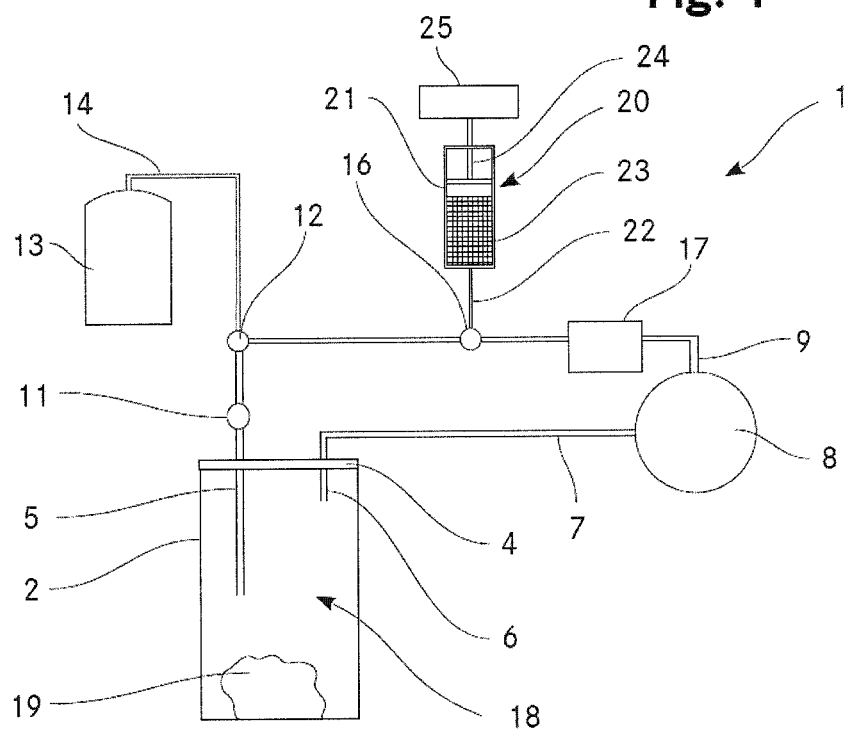
FIG. 2 shows a second embodiment of the device according to the invention with a syringe as trap element.

FIG. 2 shows a second embodiment of a device 1 according to the invention. In contrast to the embodiment according to FIG. 1, a solid sample 19 is arranged in the sample vessel 2. The gas space 18 is between the cover 4 of the sample vessel 2 and the solid sample 19. Moreover, in this embodiment, the water trap is integrated in the second fluid line 9.

A further difference is that a syringe 20 is used as trap element. The syringe comprises a barrel 21 and a needle 22, which is inserted into a port 16 located in the second fluid line 9. Arranged inside the barrel 21 is a sorption material 23 to which the volatile components are able to bind. Located above the sorption material 23 is a piston 24 with which, by an up and down movement, the volume of the gas located inside the barrel 21 can be regulated. The automatic up and down movement of the piston 24 is ensured by an actuation motor 25. By a periodic movement of the piston 24, gas from the second fluid line 9 can be sucked through the sorption material 23 and again ejected.

Instead of the port 16, a three-way valve could alternatively be used, in which case the piston 24, in the upward movement, connects the needle 22 to the pump-side part of the second fluid line 9 and, in the downward movement, connects it to the supply-side part.

The invention claimed is:

1. A device for extracting volatile components from a sample, comprising:
   a) a sample vessel for receiving the sample, wherein the sample vessel is closed in a gas-tight manner;
   b) a discharge line and a supply line, which protrude into the sample vessel, wherein the supply line has a first valve with which a flow of gas through the supply line can be throttled and/or interrupted;
   c) a pump with a suction opening and an output opening;
   d) a first fluid line which fluidically connects the discharge line to the suction opening of the pump; and
   e) a second fluid line which fluidically connects the supply line to the output opening of the pump such that the sample vessel, the supply line, the discharge line, the first fluid line, the second fluid line, and the pump form a closed gas circuit, wherein a trap element with at least one sorption material is fluidically connected to the first fluid line or the second fluid line.

2. The device according to claim 1, wherein the trap element is connected releasably to the first fluid line or the second fluid line.

3. The device according to claim 1, wherein the first fluid line or the second fluid line comprises two subsidiary fluid lines, wherein the trap element is arranged between these two subsidiary fluid lines.

4. The device according to claim 1, wherein the supply line protrudes farther into the sample vessel than the discharge line, such that, when a liquid sample is received, the supply line protrudes into the liquid sample and the discharge line protrudes into a gas space above the liquid sample.

5. The device according to claim 1, wherein, in the direction of flow of the closed gas circuit, a water trap is arranged upstream from the trap element in the first fluid line or the second fluid line.

6. The device according to claim 1, wherein the trap element has at least one valve with which the trap element can be fluidically connected to an analysis apparatus.

7. The device according to claim 1, wherein the trap element has a heating and/or cooling element.

8. The device according to claim 1, wherein the supply line can be fluidically connected to a gas reservoir via a second valve.

9. The device according to claim 1, wherein the trap element is designed as a syringe, wherein a needle of the syringe is inserted into the second fluid line, and the at least one sorption material is arranged in the barrel of the syringe.

10. A method for extracting volatile components from a sample using a device according to claim 1, said method comprising the following steps:
    a) arranging the sample in the sample vessel with a supply line and a discharge line, wherein the sample vessel is then closed in a gas-tight manner;
    b) aspirating gas out of the sample vessel, or out of a gas space located above the sample in the sample vessel, into the discharge line by the pump connected fluidically to the discharge line via the first fluid line; and
    c) the gas is conveyed by the pump into the second fluid line, which is fluidically connected to the supply line, such that the gas circulates in the sense of a closed gas circuit between sample vessel and pump, wherein volatile components of the sample, which are outgassed from the sample, are held back by the absorption material of the trap element fluidically connected to the first fluid line or to the second fluid line.

11. The method according to claim 10, wherein a gas flow of the closed gas circuit is throttled or interrupted for a predetermined time by the first valve of the supply line, such that an underpressure arises in the sample vessel and an overpressure arises in the trap element.

12. A method according to claim 10 for extracting volatile components from a sample, wherein the trap element is designed as a syringe, wherein a needle of the syringe is inserted into the second fluid line, and the at least one sorption material is arranged in the barrel of the syringe; wherein the piston of the syringe is periodically driven to and fro in the barrel.

* * * * *